(12) United States Patent
Ochoa Corona (10) Patent No.: US 9,423,398 B2
(45) Date of Patent: Aug. 23, 2016

(54) APPARATUS AND METHOD FOR BIOLOGIC SAMPLE RAPID COLLECTION AND RECOVERY DEVICE, AND CONVENIENT STORAGE

(75) Inventor: Francisco Manuel Ochoa Corona, Stillwater, OK (US)

(73) Assignee: The Board of Regents for Oklahoma State University, Stillwater, OK (US)

( * ) Notice: Subject to any disclaimer, the term of this patent is extended or adjusted under 35 U.S.C. 154(b) by 1207 days.

(21) Appl. No.: 13/023,343

(22) Filed: Feb. 8, 2011

(65) Prior Publication Data

US 2012/0202211 A1    Aug. 9, 2012

(51) Int. Cl.
*G01N 33/558* (2006.01)

(52) U.S. Cl.
CPC .................................. *G01N 33/558* (2013.01)

(58) Field of Classification Search
None
See application file for complete search history.

(56) References Cited

U.S. PATENT DOCUMENTS

| | | | |
|---|---|---|---|
| 5,496,562 | A | 3/1996 | Burgoyne |
| 5,756,126 | A | 5/1998 | Burgoyne |
| 5,807,527 | A | 9/1998 | Burgoyne |
| 6,645,717 | B1 | 11/2003 | Smith et al. |
| 7,112,358 | B1 | 9/2006 | Hacikyan |
| 2003/0091989 | A1 | 5/2003 | Davis et al. |
| 2003/0096424 | A1* | 5/2003 | Mao et al. ............... 436/169 |
| 2006/0246600 | A1* | 11/2006 | Yang et al. ............... 436/514 |
| 2007/0048182 | A1* | 3/2007 | Song et al. ............... 422/61 |
| 2007/0266777 | A1* | 11/2007 | Bergman et al. ......... 73/61.41 |
| 2008/0299005 | A1* | 12/2008 | Meathrel et al. ......... 422/56 |
| 2010/0290948 | A1* | 11/2010 | Song ....................... 422/56 |
| 2011/0117540 | A1* | 5/2011 | Cary ....................... 435/5 |
| 2011/0117636 | A1* | 5/2011 | Bae et al. ................ 435/287.2 |
| 2011/0306120 | A1* | 12/2011 | Nicholls et al. .......... 435/287.2 |
| 2012/0132560 | A1* | 5/2012 | Hulka et al. ............. 206/524.6 |
| 2012/0270225 | A1* | 10/2012 | Wakeley et al. ......... 435/6.12 |

FOREIGN PATENT DOCUMENTS

WO    WO 2011051562 A1 * 5/2011

OTHER PUBLICATIONS

Hossain et al. (Development of a Bioactive Paper Sensor for Detection of Neurotoxins Using Piezoelectric Inkjet Printing of Sol-Gel-Derived Bioinks, Anal. Chem. 2009, 81, 5474-5483).*
"Elution" Wikipedia entry, "www.en.wikipedia.org/wiki/Elution", publication date unknown.
Nic, M. et al., "Eluent", Compendium of Chemical Terminology, 2nd ed. (the 'Gold Book'), published 2006, Publisher: IUPAC.
Kadokami, Y. et al., "Membrane bound PCR", Nucleic Acids Research, Apr. 6, 1990, p. 3082 vol. 18, No. 10, Publisher: Oxford University Press.
Maskell, D. et al., "PCR amplification of DNA sequences from nitrocellulose-bound, immunostained bacterial colonies", Nucleic Acids Research, Nov. 24, 1992, pp. 171-172, vol. 21, No. 1, Publisher: Oxford University Press.
Sheikh, S. et al., "Re-usable DNA template for the polymerase chain reaction (PCR)", Nucleic Acids Research, Jul. 7, 1997, pp. 3537-3542, vol. 25, No. 17, Publisher: Oxford University Press.

* cited by examiner

*Primary Examiner* — Aaron Priest
(74) *Attorney, Agent, or Firm* — Fellers, Snider, Blankenship, Bailey & Tippens, P.C.; Terry L. Watt (57) ABSTRACT

In accordance with exemplary embodiments, apparatus and method for biologic sample rapid collection and recovery device, and convenient storage are provided. An exemplary embodiment includes an apparatus comprising a lateral flow technology device including at least a membrane configured to bind an analyte from a sample that flows through the lateral flow technology device, in which a selected portion of the membrane bound to the analyte when placed directly in an analysis system does not substantially inhibit analysis of the analyte. An elution protocol is not required to extract the analyte bound from the selected portion before placed directly in the analysis system.

6 Claims, 7 Drawing Sheets

APPARATUS AND METHOD FOR BIOLOGIC SAMPLE RAPID COLLECTION AND RECOVERY DEVICE, AND CONVENIENT STORAGE

FIELD OF THE INVENTION

This invention relates to apparatus and method for biologic sample rapid collection and recovery device, and convenient storage that includes, but is not limited to, collecting, storing and recovering nucleic acid from a microorganism.

BACKGROUND

Polymerase chain reaction ("PCR") is a powerful molecular biology technique used to copy, i.e., amplify, specific nucleic acid sequences within template deoxyribonucleic acid ("DNA"), whether derived from native DNA or cDNA reverse transcribed from ribonucleic acid ("RNA"). An entire PCR assay is carried out in a single tube containing a mixture of enzyme, template, primers, and substrates. Each amplification cycle starts with denaturation (which includes at least heating) that is followed by annealing and then elongation (also known as synthesis and polymerization) reactions.

The PCR assay, in which the cycle of denaturing, annealing and synthesizing reactions is typically repeated 20 or more times, can be divided into three phases: exponential when the PCR reaction product doubles during every cycle (assuming 100% reaction efficiency); linear when the reaction components are consumed, and the reaction product growth slows and degrades; and plateau when the reaction product growth stops and degrades. In traditional (also known as End-Point, or classic) PCR, detection and quantitation of the amplified sequence, i.e., the reaction product, are performed in the plateau phase. In real-time PCR, the amount of PCR reaction product is detected and measured at each cycle during the exponential growth phase, which enables determination of the initial amount of DNA template with great precision.

Enzyme-linked immunosorbent assay ("ELISA") is a commonly used diagnostic technique, in which an enzyme is coupled directly to an antibody. The antibody bound to an unknown amount of antigen can be quantitated indirectly by measuring the conversion by the enzyme of an ELISA substrate to a product. A detectable signal can permit real-time determination of the ELISA reaction rate, e.g., a color change can be used to quantify enzyme reaction through photometric adsorbency measurement.

Lateral flow technology ("LFT") assay (also known simply as strip-test) has been a popular platform for diagnostic tests since its introduction in the late 1980s, e.g., the human early pregnancy test. LFT assay has been used for qualitative or semi-quantitative detection of specific analytes including antigens and antibodies, hence other common names for LFT assay: lateral flow immunoassay and immunochromatographic strip test. Biologic sample for LFT assay may be derived from whole blood, serum, plasma, saliva, urine, feces, wound exudate, soil, dust, vegetation, food, or other suitable source. Even products of nucleic acid amplification systems, such as PCR reaction products, can be studied by LFT assay. LFT assay can be run in a single step using the biologic sample in a variety of test locations, such as laboratory, agricultural field, crime scene, etc. Several analytes can be tested simultaneously on the same strip.

The prior art requires a burdensome and time consuming step of eluting (also known as extracting) an analyte from an LFT device before performing the PCR or ELISA technique on the analyte collected by LFT assay. There exists a need in the art for an LFT device configured for collecting (also known as sampling, fixing, or binding) the analyte that may be placed directly in an analysis system for analysis, such as by the PCR or ELISA technique, without the eluting step intervening. Eliminating the eluting step would speed and simplify the collection of specimens for molecular-clinical diagnostics. The apparatus and method embodied by the claims finds application when sampling specimens for molecular-clinical diagnostics in human health, veterinary health, plant health, biosecurity (e.g., surveillance and response), defense, forensics, microbial forensics, and food quality and biosecurity, among other fields of study.

SUMMARY OF THE INVENTION

In accordance with exemplary embodiments, apparatus and method for biologic sample rapid collection and recovery device, and convenient storage are provided.

An exemplary embodiment includes an apparatus comprising a lateral flow technology ("LFT") device including at least a membrane configured to bind an analyte from a sample that flows through the LFT device, in which a selected portion of the membrane bound to the analyte when placed directly in an analysis system does not substantially inhibit analysis of the analyte.

An alternative exemplary embodiment includes an apparatus comprising an LFT system including at least a membrane configured to bind an analyte from a sample that flows through the LFT system, such that the LFT system facilitates a period of storage of the analyte bound to the membrane and does not substantially inhibit analysis of the analyte bound to the membrane when placed in an analysis system after the period of storage.

Another exemplary embodiment includes a method comprising, the steps of: flowing a sample solution that contains an analyte through an LFT device configured to bind the analyte; punching a sample disc that binds the analyte from the LFT device; and placing the sample disc directly in an analysis system for analysis of the analyte, in which the step of placing the sample disc is not preceded by a step of eluting the analyte from the sample disc.

These and various other features and advantages that characterize the claimed invention will be apparent upon reading the following detailed description and upon review of the associated drawings.

DETAILED DESCRIPTION OF EXEMPLARY EMBODIMENTS

Detailed descriptions of the exemplary embodiments are provided herein. It is to be understood, however, that the invention embodied in the claims may take various forms. Various aspects of the invention may be inverted, or changed in reference to specific part shape and detail, part location, or part composition. In addition, the figures shown are not drawn to scale. Therefore, specific details disclosed herein are not to be interpreted as limiting, but rather as a basis for the claims and as a representative basis for teaching one skilled in the art to employ the invention embodied in the claims in virtually any appropriately detailed system, structure or manner.

OVERVIEW

Figures 1, 1A:
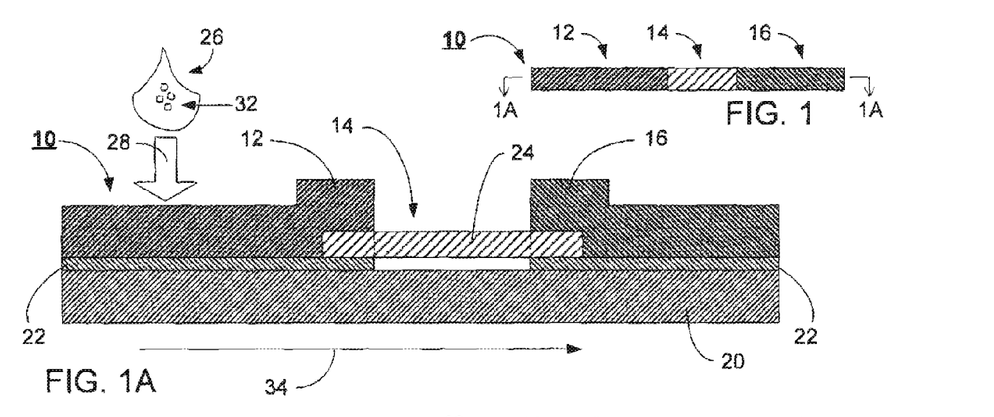
FIG. 1 shows plan view of an exemplary lateral flow technology device.
FIG. 1A illustrates a sectional view taken along the line 1A-1A of FIG. 1.

FIG. 1 shows an exemplary configuration of a lateral flow technology ("LFT") device 10 that includes at least a sample pad 12, a membrane 14, and a wick 16. FIG. 1A sectional view depicts the sample pad 12, the membrane 14, and the wick 16 overlap one another and are mounted on a backing card 20, such as with an adhesive 22, e.g., a pressure-sensitive adhesive, therebetween. In one embodiment a MIBA-020 backing card with an adhesive coating is used. As discussed below, it has been found that an unmounted portion 24 of the membrane 14 produces useful characteristics.

An LFT assay is run by bringing a sample 26 in contact, e.g., in a sample application direction 28, with the sample pad 12 of the LFT device 10. The sample 26 flows (in a flow direction 34) through the sample pad 12 into the membrane 14. Some portion of an analyte 32 in the sample 26 may become fixed in the membrane 14. The sample 26, including the analyte 32, not fixed to the membrane 14 flow (in the flow direction 34) towards the wick 16 where the sample 26, including the analyte 32, are entrapped (also known as absorbed). In certain embodiments, the sample 26 is a biologic sample and the analyte 32 is nucleic acid from a microorganism.

Figures 2, 2A:
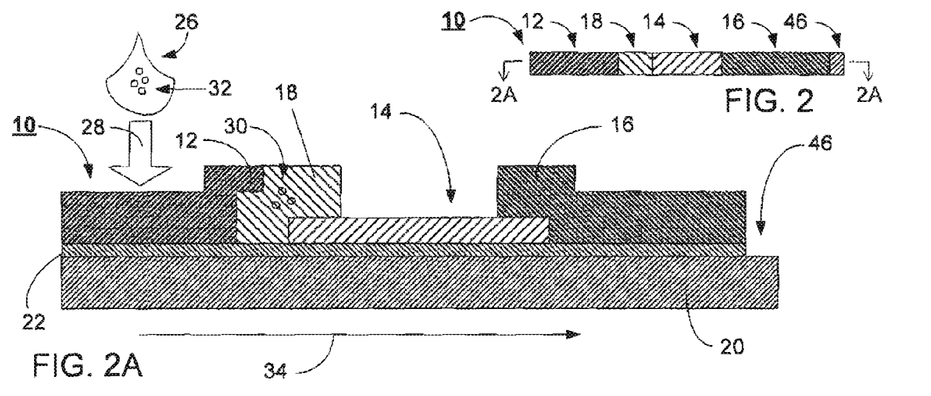
FIG. 2 shows plan view of another exemplary lateral flow technology device.
FIG. 2A illustrates a sectional view taken along the line 2A-2A of FIG. 2.

FIG. 2 shows another exemplary embodiment of the LFT device 10 with a conjugate pad 18 disposed between the sample pad 12 and the membrane 14. As illustrated in the FIG. 2A sectional view, the LFT assay is run by bringing the sample 26 in contact, e.g., in the sample application direction 28, with the sample pad 12 of the LFT device 10. The sample 26 flows (in the flow direction 34) through the sample pad 12 to the conjugate pad 18, where the particulate conjugate 30 has been immobilized. The sample 26 mobilizes the particulate conjugate 30, and the analyte 32 in the sample 26 interacts with the particulate conjugate 30 as they flow (in the flow direction 34) into the membrane 14. Some portion of the particulate conjugate 30 and the analyte 32 may become fixed in the membrane 14. The excess of the sample 26, including the analyte 32, and the particulate conjugate 30 not fixed to the membrane 14 flow (in the flow direction 34) towards the wick 16 where they are entrapped. The conjugate pad 30 is optional.

Figures 3, 3A:
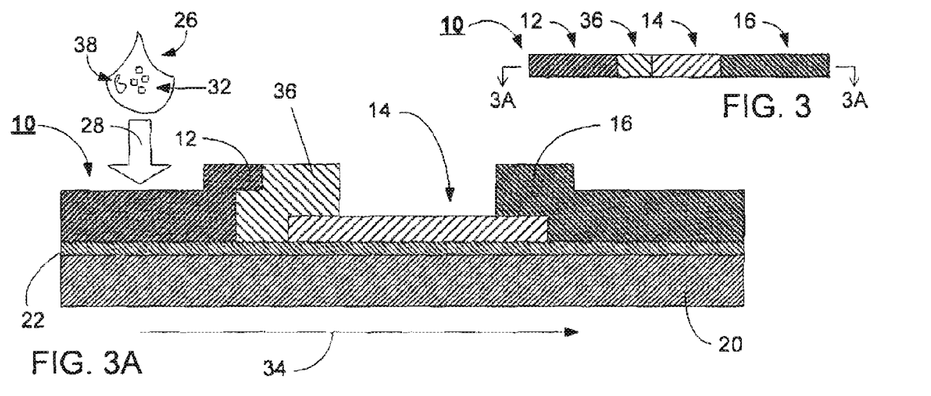
FIG. 3 shows plan view of an alternate exemplary lateral flow technology device.
FIG. 3A illustrates a sectional view taken along the line 3A-3A of FIG. 3.

FIG. 3 portrays an alternative embodiment of the LFT device 10, in which a specimen filter 36 is disposed between the sample pad 12 and the membrane 14. As shown in the FIG. 3A sectional view, the specimen filter 36 is configured to collect a sample debris 38 from the sample 26 while allowing the analyte 32 to flow (in the flow direction 34) from the sample pad 12 through the specimen filter 36 to the membrane 14 and into the wick 16 when the sample 26 is brought in contact, e.g., in the sample application direction 28, with the sample pad 12 of the LFT device 10. The absorbed fluid of the sample 26 flows (in the flow direction 34) through the specimen filter 36 to help separate the specimen fractions, e.g., the analyte 32, and cell debris, e.g., the sample debris 38, by size. The specimen filter 36 is optional.

FIGS. 1-3A demonstrate various embodiments; however, it will be understood that alternative embodiments can be utilized, e.g., any embodiment may or may not have the unmounted portion 24 of the membrane 14. Similarly, any of the various embodiments can have the holder 46 (as shown in FIGS. 2-2A) configured for handling the LFT device 10 or providing a label space for the LFT device 10.

Lateral Flow Technology Assay Formats

The LFT device 10 can further include either direct (also known as sandwich technique), competitive (also known as inhibition technique), or "boulders in the stream" format LFT assay, as readily known to those skilled in the art. However, these assay formats are optional.

Figure 4A:
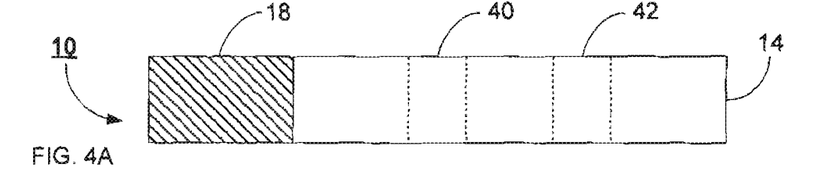
FIG. 4A portrays a plan view of a portion of an exemplary direct format lateral flow technology assay before the assay is run.
Figure 4B:
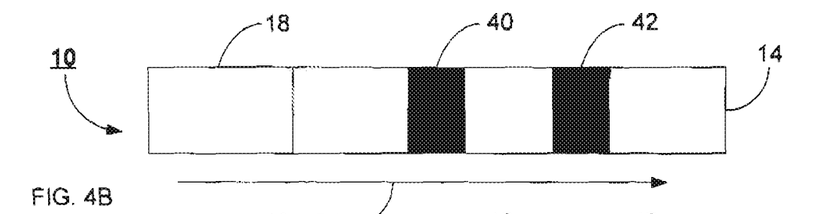
FIG. 4B depicts a plan view of a portion of the exemplary direct format lateral flow technology assay after the assay is run and the result is positive.
Figure 4C:
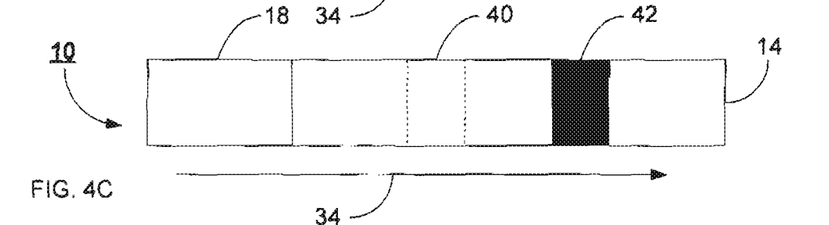
FIG. 4C reveals a plan view of a portion of the exemplary direct format lateral flow technology assay after the assay is run and the result is negative.

FIGS. 4A-C illustrate a portion of the LFT device 10 showing the conjugate pad 18 and the membrane 14. FIG. 4A represents the LFT device 10 before the direct format LFT assay is run. FIG. 4B shows the LFT device 10 after the assay is run (in the flow direction 34) for a positive result. A test line 40 is visible (depicted as black) and a control line 42 is visible. FIG. 4C portrays the LFT device 10 after the assay is run (in the flow direction 34) for a negative result. The test line 40 is invisible (depicted as bounded by broken lines) and the control line 42 is visible.

Figure 5A:
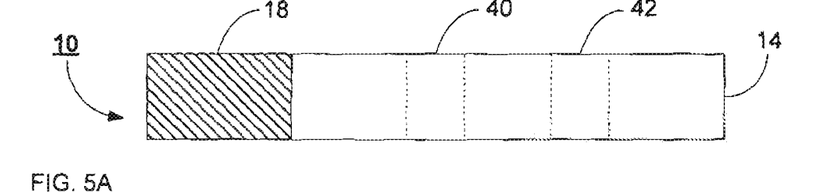
FIG. 5A portrays a plan view of a portion of an alternate exemplary competitive format lateral flow technology assay before the assay is run.
Figure 5B:
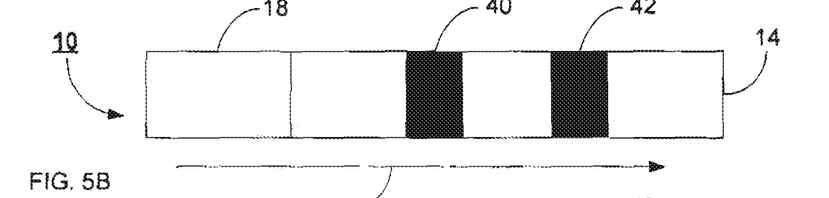
FIG. 5B depicts a plan view of a portion of the alternate exemplary competitive format lateral flow technology assay after the assay is run and the result is negative.
Figure 5C:
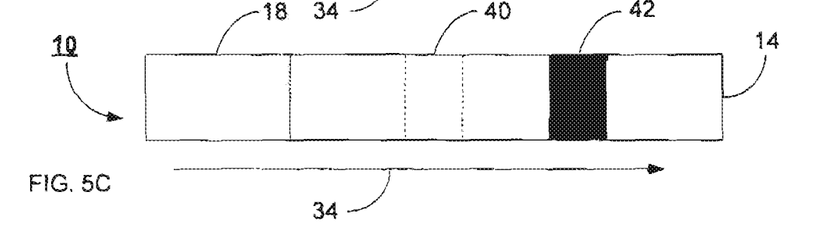
FIG. 5C reveals a plan view of a portion of the alternate exemplary competitive format lateral flow technology assay after the assay is run and the result is positive.

FIGS. 5A-C illustrate a portion of the LFT device 10 showing the conjugate pad 18 and the membrane 14. FIG. 5A represents the LFT device 10 before the competitive format LFT assay is run. FIG. 5B shows the LFT device 10 after the assay is run (in the flow direction 34) for a negative result. The test line 40 is visible and the control line 42 is visible. FIG. 5C portrays the LFT device 10 after an assay is run (in the flow direction 34) for a positive result. The test line 40 is invisible and the control line 42 is visible.

Further details regarding LFT technology are given below, and the book *Lateral Flow Immunoassay* edited by Raphael Wong and Harley Tse, Humana Press (2009) provides further information and is incorporated by reference herein.

Membrane

One purpose of the membrane 14 (also known as analytical region, reaction membrane, or matrix membrane) in the LFT device 10 is to bind the analyte 32, such as protein, antigen, antibody, nucleic acid, or microorganism.

Traditionally, nitrocellulose has been the material of choice for the membrane 14 in the vast majority of LFT devices 10. Other traditional materials for the membrane 14 have included nylon and polyvinylidene fluoride. Nitrocellulose has flaws, such as flammability and breakage problems when the membrane 14 does not adhere to the backing card 20. The traditional materials have shelf-life longevity issues. In addition, the analyte 32 sampled by the LFT device 10 must be extracted from the membrane 14 made of these traditional materials (nitrocellulose, nylon, polyvinylidene fluoride, etc.) by the burdensome and time-consuming process of elution in order for the analyte 32 to be analyzed in an analysis system, such as those using the PCR or ELISA technique, such as is described in (I) IUPAC Gold Book: eluent. International Union of Pure and Applied Chemistry, www.goldbook.iupac.org/E02040.html. Retrieved 2008-09-28; (2) Brown, Phillis (2001). Advances in chromatography. CRC Press. pp. 36. ISBN 082470509; and (3) Elution. www.en.wikipedia.org/wiki/Eiution; each of which are hereby incorporated by reference.

However, it has been found that by selecting an appropriate material that does not substantially inhibit (or interfere with or impede) PCR, the membrane 14 may be placed directly into End-Point PCR mixtures, reverse transcription PCR mixtures, real-time PCR mixtures, without the eluting step intervening and variants of these methods. Alternatively, the membrane 14 may be placed directly, without the eluting step intervening, in an analysis system using the ELISA technique. In other words, the membrane 14 collects the analyte 32 in the LFT device 10 when the LFT assay is run, and the membrane 14 acts a carrier of the analyte 32 into the PCR or ELISA system, or other suitable analysis system.

Figure 6:
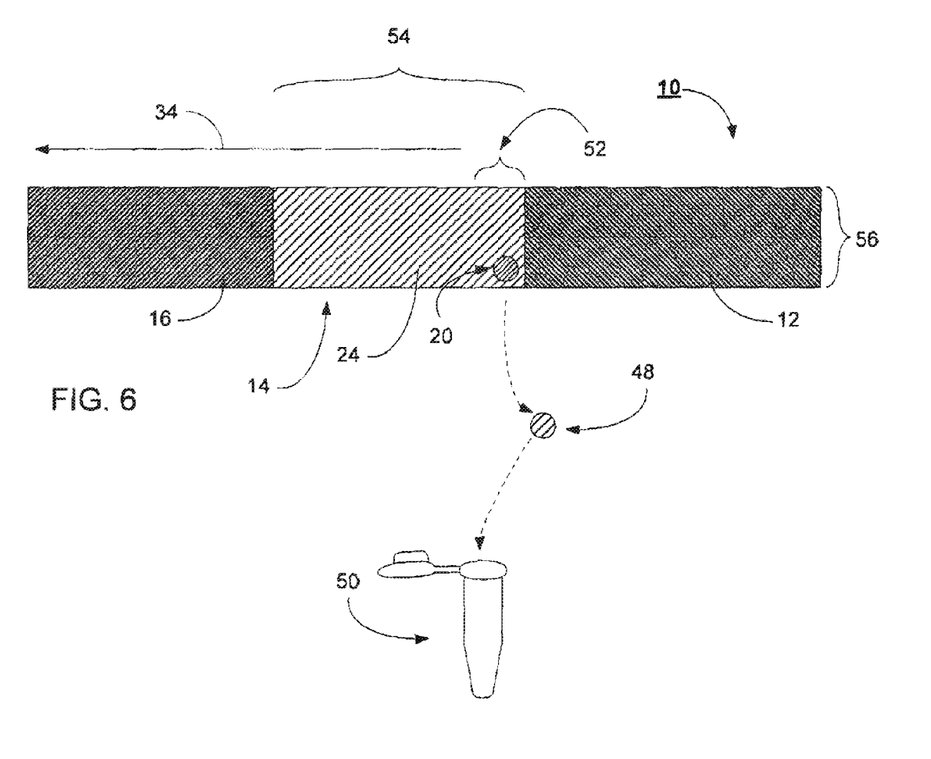
FIG. 6 shows an exemplary embodiment where a selected portion of the membrane is placed directly in a PCR test tube of an analysis system.

As shown in FIG. 6, after the LFT assay has been run (in the flow direction 34) from the sample pad 12 to the wick 16, a membrane disc (also known as a "punch" or "selected portion" or "sample disc") 48 is obtained from the membrane 14 made of a suitable biomaterial in an exemplary embodiment. The punch 48 is a selected portion of the membrane 14, e.g., 1.2 millimeter ("mm") diameter piece obtained with a Whatman® Harris Uni-Core™ 1.2 mm ("puncher"), which is placed directly into a PCR tube (depicted as 50) or an ELISA microplate well of the PCR or ELISA analysis system, respectively. Other suitable sizes and shapes for the punch 48 may be used in various embodiments.

In a particular exemplary embodiment, the membrane 14 is made from a water soluble paper, e.g., Aquasol® Water Soluble Paper is a unique product made of sodium carboxy methyl cellulose ("SCMC") and wooden pulp that dissolves in cold water, hot water, steam and most aqueous solutions. In addition, Aquasol® Water Soluble Paper is described as nontoxic, environmentally friendly, and 100% biodegradable. Aquasol® Water Soluble Paper can be obtained from Aquasol Corporation (North Tonawanda, N.Y. USA).

Water soluble paper containing SCMC is available in a variety of SCMC cards that can be used to make the membrane 14. SCMC cards evaluated for the membrane 14 are ASW-15, which has 50 μm thickness; ASW-25, which has 83 μm thickness; ASW-50, which has 76 μm thickness; ASW-DC, which has 50 μm thickness; and ASW-240, which has 170 μm thickness. However, other material with suitable characteristics disclosed may be utilized for the membrane 14. The more preferred SCMC cards from the above five SCMC cards are ASW-15, ASW-25 and ASW-50, because these SCMC cards did not substantially inhibit PCR up to a fifth order of magnitude dilution of a test using plasmid-fungal DNA. The starting solution is diluted four times for a total of five concentrations, i.e., A=10 ng/μl; B=1 ng/μl; C=0.1 ng/μl; D=0.01 ng/μl; E=0.001 ng/μl; F=is negative control, water only no DNA.

Conjugate Pad

The role of the conjugate pad 18 (as shown in FIGS. 2-2A) in the LFT device 10 includes accepting the particulate conjugate 30, holding the particulate conjugate 30 stable over shelf life (preferably up to 2 years) of the LFT device 10, and releasing the particulate conjugate 30 efficiently and reproducibly when the LFT assay is run. As the skilled artisan will know, it is often necessary to pretreat the conjugate pad 18 to assure optimal release and stability of the particulate conjugate 30.

Materials of choice for the conjugate pad 18 are glass fiber, polyester or Rayon. In an exemplary embodiment, the conjugate pad 18 is made from nitrocellulose. For the best results, the materials for the conjugate pad 18 should be hydrophilic and allow rapid flow rates.

The particulate conjugate 30 may be adsorbed with antibodies or antigens that are specific to the analyte 32 to be collected. A label for the particulate conjugate 30 may include colloidal gold or monodisperse latex, tagged with either a visual or a fluorescent dye. The labels can be read qualitatively or quantitatively after the assay is run.

As previously mentioned, the conjugate pad is optional.

Sample Pad

The role of the sample pad 12 (e.g., as shown in FIGS. 1-3A and 6) in the LFT device 10 includes accepting the sample 26, treating the sample 26 such that it is compatible with the LFT device 10, and releasing with high-efficiency the analyte 32 into the rest of the LFT device 10, e.g. the membrane 14. The sample pad 12 must be able to accept in a controlled way all of the fluid volume from the sample 26, thereby helping to channel the fluid into the assay materials (such as the conjugate pad 18, the membrane 14, and the wick 16) rather than allowing flooding or surface flow. Sample treatments for the sample pad 12 include filtering unwanted particulates, changing the pH, binding sample components that can inhibit running the LFT assay, and disrupting sample components, such as mucins, to release the analyte 32 to the LFT device 10. In some embodiments, the sample pad 12 and the conjugate pad 18 can be the same component.

Tensile strength while the sample pad 12 is wet from the sample 26 is an important criterion used in selecting the material for the sample pad 12. In an exemplary embodiment, the fluid volume of the sample 26 used to run the LFT assay is 0.5 milliliters ("ml"), or 500 microliters ("μl").

Examples of materials used for the sample pad 12 are cellulose, glass fiber, Rayon, and other filtration media. In exemplary embodiments, the sample pad 12 is made from Whatman GB002, Standard 17, or GF33 (from Whatman plc, UK); or Millipore C083 (from Millipore in Billerica, Mass. USA).

Wick

The wick 16 (e.g., as shown in FIGS. 1-3A and 6) acts as the engine of the LFT device 10 while running the LFT assay to pull fluid from the sample 26 added to the LFT device 10 into the wick 16 and hold the fluid for the duration of the assay and in an exemplary embodiment for the duration of storage until recovery of the analyte 32 by the punch 48 from the membrane 14. The wick 16 should not release fluid back into the membrane 14 or false positive results may occur.

The wick 16 is typically made from high-density cellulose, which is generally selected for absorptive capacity and tensile strength. An exemplary wick 16 is made from Millipore C083.

"Wicking rate" or "capillary rise time" is defined as the time required for a fluid front of the sample 26 to traverse the distance from the sample pad 12 through the membrane 14 to absorption at the wick 16. Wicking rate is an important criterion when selecting the materials for making the sample pad 12, the membrane 14, the wick 16, etc. In an exemplary embodiment, the wicking rate is chosen to be less than the time for the membrane 14 made from water soluble paper to dissolve in the fluid of the sample 26.

Specimen Filter

The role of the specimen filter 36 (as shown in FIGS. 3-3A) is separation of the specimen fractions, e.g., the analyte 32, and the cell debris, e.g., the sample debris 38. The specimen filter may be made from a variety of materials known to one skilled in the art. In an exemplary embodiment, the specimen filter 36 is made from nitrocellulose.

The specimen filter 36 is optional. The sample pad 12 may provide some of the filtration function that could be provided by the specimen filter 36.

Backing Card

The role of the backing card 20 (as shown in FIGS. 1A, 2A, and 3A) includes providing rigidity to the LFT device 10, which eases handling of the LFT device. The backing card 20 can be made from polystyrene or other plastics, or other suitable material. In an exemplary embodiment, the backing card 20 is made from Part # MIBA-020 obtained from Diagnostic Consulting Network (Carlsbad, Calif. USA).

Next, actual examples of the LFT device and components are described below.

Exemplary Lateral Flow Device

Figure 7:
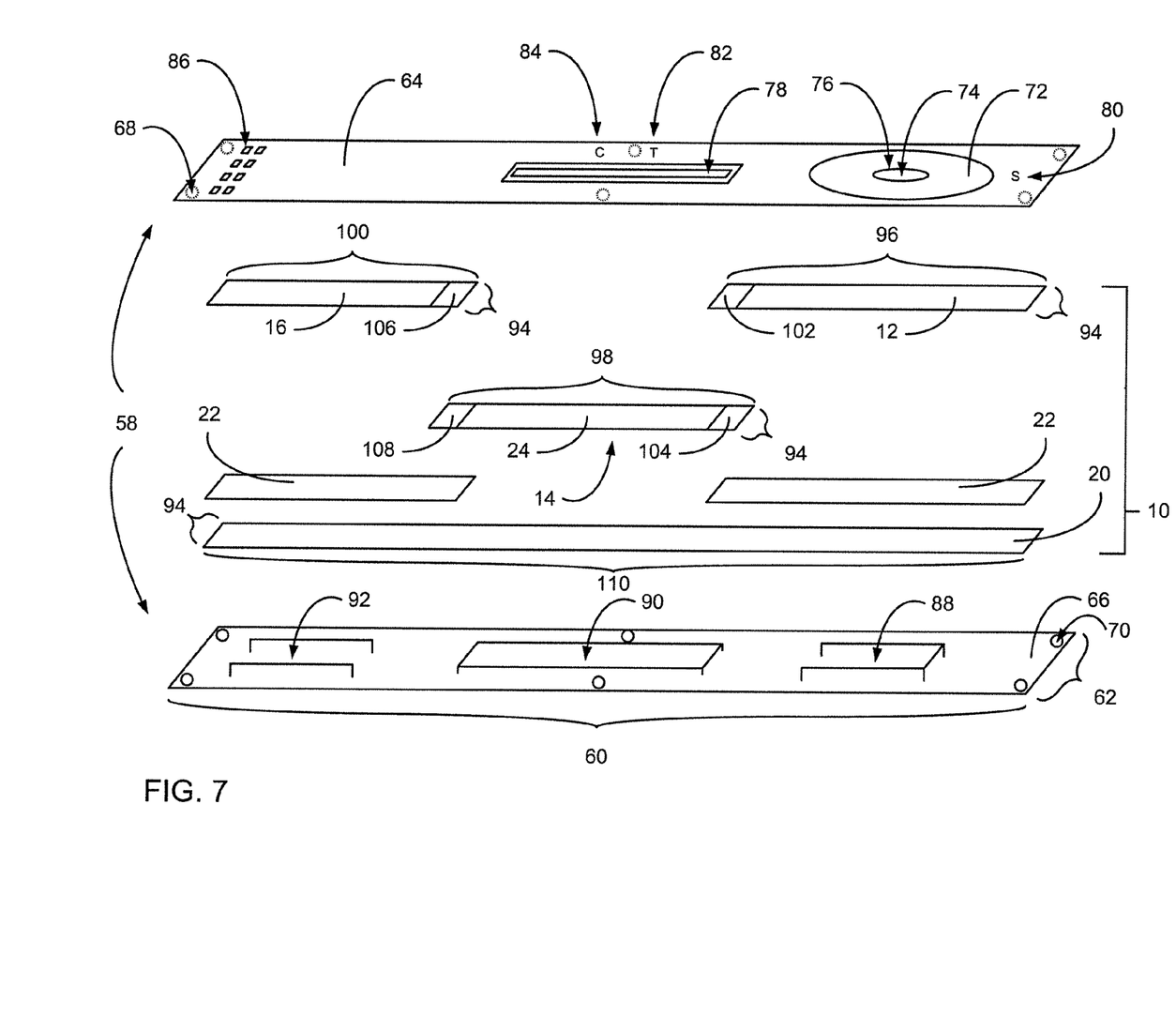
FIG. 7 shows an exploded view of an exemplary lateral flow technology device with an optional cassette.

FIG. 7 portrays an exemplary embodiment in exploded view of the LFT device 10 surrounded by a cassette (also known herein as "housing") 58. The sample pad 12 and wick 16 are made from Millipore C083. The membrane 14 is made from Aquasol ASW-25. The backing card 20 is made from MIBA-020. The fluid volume of the sample 26 used for the exemplary embodiment is 0.5 ml. The wicking rate is approximately 3 minutes, i.e., 2.94 minutes, as measured by the mean of ten test runs of the sample 26 through the LFT device 10 for the time required for a fluid front of the sample 26 to traverse from the bottom of the sample pad 12 to the top of specimen filter, i.e., a 50 mm travel distance. The average speed is 17 mm/min.

In the exemplary embodiment, the plastic cassette 58 is MICA-0120 sold by Diagnostic Consulting Network (Carlsbad, Calif.), herein incorporated by reference. The outside length 60 of the plastic cassette 58 is 69 mm. The outside width 62 of the plastic cassette 58 is a cassette width of 20 mm. The cassette 58 is optional.

In the exemplary embodiment, the cassette 58 has an upper housing member 64 and a lower housing member 66. The upper housing member 64 has an attachment element 68 (shown in partial cutaway) and correspondingly the lower housing member 66 has an engagement element 70. The attachment element 68 and the engagement member 70 may be reversed between the upper housing member 64 and the lower housing member 66. The attachment element 68 can reversibly engage the engagement element 70 for containment of the LFT device 10 by the housing 58. The upper housing member 64 and the lower housing member 66 may have a plurality of attachment elements 68 and engagement elements 70, respectively.

The upper housing member 64 has a well 72 for receiving fluid from the sample 26 and a well aperture 74 at the base of the well 72 for releasing fluid into the sample pad 12. The well 72 may receive 0.5 ml of fluid without overflowing. A rim 76 of the well aperture 74 may be biased into the sample 12 when the cassette 58 contains the LFT device 10 so that fluid from the sample 26 does not flood or surface flow the LFT device 10.

The upper housing member 64 has a membrane window 78 through which LFT assay results may be viewed without opening the cassette 58 containing the LFT device 10. In addition, the punch 48 from the membrane 14 can be obtained without opening the cassette 58. In the MIBA-0120, S (labeled 80) for the sample 26, T (labeled 82) for the test line 40, and C (labeled 84) for the control line 42 are provided. A gripping area 86 is provided, also.

The lower housing member 66 has a sample guide 88 that facilitates biasing the sample pad 12 towards the well aperture 74 when the LFT device 10 is contained within the cassette 58. The pedestal 90 facilitates biasing the membrane 14 towards the membrane window 78 when the LFT device 10 is contained within the cassette 58, which promotes efficiently obtaining the punch 48. A wick guide 92 provides lateral support to the LFT device 10 adjacent the wick 16 to help maintain positions of the sample pad 12 and the membrane 14 relative to the well aperture 74 and the membrane window 78, respectively.

In the exemplary embodiment of the LFT device 10, the width 94 of each of the sample pad 12, the membrane 14, the wick 16, and the backing card 20 is 4 mm; the length 96 of the sample pad 12 is 26 mm; the length 98 of the membrane 14 is 25 mm; the length 100 of the wick 16 is 21 mm; and the length 110 of the backing card 20 is 67 mm. The sample pad 12 has an unmounted portion 102 that overlaps the membrane 14 by 2.5 mm at the first end 104 of the membrane 14. The remaining 23.5 mm of the sample pad 12 is mounted to the backing card 20 by the adhesive 22. The wick 16 has an unmounted portion 106 that overlaps the membrane 14 by 2.5 mm at the second end 108 of the membrane 14. The remaining 18.5 mm of the wick 16 is mounted to the backing card 20 by the adhesive 22. The first end 104 and the second 108 are mounted to the backing card 20 by the adhesive 22, while the unmounted portion 24, which in this exemplary embodiment has a length of 20 mm, of the membrane 14 is not adherent to the backing card 20.

The unmounted portion 24 facilitates obtaining the punch 48 (as shown in FIG. 6) of the membrane 14 without the backing card 20 (shown in FIG. 6) adherent. The punch 48 thus obtained may be placed directly in the analysis system for analysis of the analyte 32 without first needing to elute the analyte 32 from the punch 48, when the backing card 20 adherent to the punch 48 could interfere with analysis of the analyte 32.

When the plurality of attachment members 68 of the upper housing member 64 are correspondingly coupled to the plurality of the engagement members 70 of the lower housing member 66 upon closing the plastic cassette 58, the LFT device 10 is held relatively immobile in a protective container that promotes convenient storage. In preferred embodiments, the LFT device 10 conveniently stores the analyte 32 collected on the membrane 14 for at least 1 month, 3 months, 6 months, 12 months, 18 months, or 24 months at room temperature (~23° C.), in a refrigerator (~4° C.), in a freezer (~−20° C.), or in a deep freezer (~−80° C.), or in some combination of temperatures. To present positive storage has been determined for eight months for types of soluble membrane at all temperatures. Considering the observed good yields of DNA it is projected at least 24 months of storage. After the convenient storage, the analyte 32 is reliably recovered by the punch 48 and carried to the analysis where the analyte 32 is analyzed in the analysis system.

In other words, an exemplary embodiment of an apparatus has an LFT system including at least a membrane 14 configured to bind an analyte 32 from a sample 26 that flows through the LFT system, such that the LFT system facilitates a period of storage of the analyte 32 bound to the membrane 14 and does not substantially inhibit analysis of the analyte 32 bound to the membrane 14 when placed in an analysis system after the period of storage. A second embodiment includes a selected portion 48 of the membrane 14 is water soluble paper placed directly in the analysis system for analysis of the analyte 32. A third embodiment includes the period of storage is substantially at a predetermined temperature chosen from a group consisting of room temperature, refrigeration, freezing, and deep freezing. A fourth embodiment includes the period of storage is at least 3 months before the selected portion 48 is placed directly in the analysis system, and the analysis system includes at least an analysis technique selected from a group consisting of PCR and ELISA.

Punch from Water Soluble Paper

It has been found that the appropriately selected membrane 14 can capture the analyte 32 of interest, yet still present the analyte 32 for analysis in the analysis system while not substantially inhibiting the analytic technique. An exemplary embodiment of such a membrane 14 is water soluble paper. Various water soluble papers with different thicknesses were tested. It was found that the thickest material has more residue as seen by higher absorption reading. In addition, the thickest material absorbed water faster than the thinnest material. The application of water produced no perforation, fissures, cracking, holes or breakage in the water soluble paper even with the test water volume increased to 10 μl.

A scanning electron microscope ("SEM") was used to determine the surface appearance of water soluble paper in the previously wet versus dry states, and to assess water soluble paper looking for the presence of pore spaces, or crevices, that may serve as storage pockets for the analyte 32, such as a microorganism or nucleic acid. A small piece of water soluble paper (dry versus previously wet by 10 μL water then allowed to dry) was treated with gold-palladium coating and viewed under SEM at magnification=100×, Spot=3.0, and HV=10.00 kV. It was found that the organization of the paper fibers in the previously wet water soluble paper is more scattered than in the dry water soluble paper.

Figure 8:
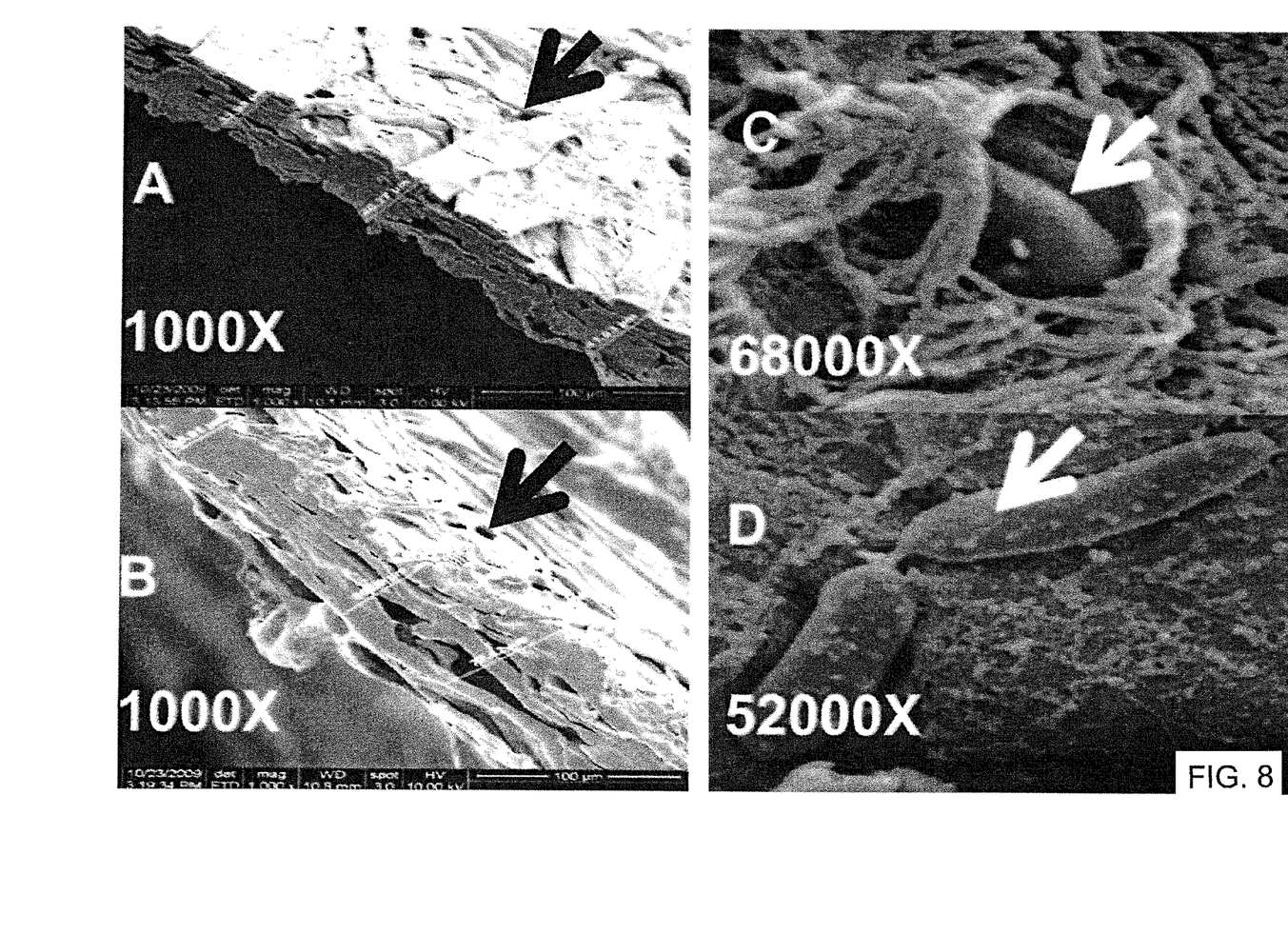
FIG. 8 shows an SEM picture of bacteria on water soluble paper.

The water soluble paper was studied for the ability to bind (or fix) bacteria, i.e., analyte 32, to the soluble paper using SEM analysis. Due to the solubility properties of water soluble paper, fixation of bacteria 32 in water soluble paper had some challenges. However, bacteria 32 could be trapped in the water soluble paper, particularly in the crevices (see FIG. 8).

An embodiment includes a storage crevice of the membrane 14 configured to bind the analyte 32. A second embodiment includes the storage crevice is absent before the sample flows through the membrane 14.

In a particular exemplary embodiment, the membrane 14 is made from a water soluble paper, e.g., Aquasol® Water Soluble Paper is a unique product made of sodium carboxy methyl cellulose ("SCMC") and wooden pulp that dissolves in cold water, hot water, steam and most aqueous solutions. Water soluble paper containing SCMC is available in a variety of SCMC cards that can be used to make the membrane 14. SCMC cards evaluated for the membrane 14 are ASW-15, ASW-25, ASW-50, ASW-DC, and ASW-240. However, other material with suitable characteristics disclosed may be utilized for the membrane 14. The more preferred SCMC cards from the above five SCMC cards are ASW-15, ASW-25 and ASW-50, because these SCMC cards did not substantially inhibit PCR up to a fifth order of magnitude dilution of a test using plasmid-fungal DNA. The starting solution is diluted four times for a total of five concentrations, i.e., A=10 ng/μl; B=1 ng/μl; C=0.1 ng/μl; D=0.01 ng/μl; E=0.001 ng/μl; F=is negative control, water only, no DNA.

The punch 48 taken from the unmounted portion 24 of membrane 14 (as also seen in FIG. 1A) can be placed directly into the analysis system when the membrane 14 is made from material that does not interfere with the analysis technique, such as the PCR or ELISA technique. Thus, the exemplary embodiment yields a robust apparatus and method for biologic sample that reduces, and may eliminate, the need of tedious extraction protocols for the analyte 32.

In other words, an exemplary embodiment is an apparatus having an LFT device 10 including at least a membrane 14 configured to bind an analyte 32 from a sample 26 that flows through the LFT device 10, in which a selected portion 48 of the membrane 14 bound to the analyte 32 when placed directly in an analysis system does not substantially inhibit analysis of the analyte 32. A second embodiment includes an elution protocol is not required to extract the analyte 32 bound from the selected portion 48 before placed directly in the analysis system. A third embodiment includes the selected portion 48 of the membrane 14 is water soluble paper. A fourth embodiment includes the analysis system includes at least an analysis technique selected from a group consisting of PCR and ELISA. A fifth embodiment includes the selected portion 48 of the membrane 14 includes at least sodium carboxy methyl cellulose. A sixth embodiment includes the selected portion 48 of the membrane 14 bound to the analyte 32 is placed directly in the analysis system without elution of the analyte 32 from the membrane 14, and the analysis system includes at least an analysis technique selected from a group consisting of PCR and ELISA.

In another embodiment, the LFT device 10 further comprises at least a backing card 20 adherent to a mounted portion (such as first 104 or second end 108) of the membrane 14, in which the membrane 14 includes the mounted portions (104, 108) and an unmounted portion 24 that is not adherent to the backing card 20, and the selected portion 48 is selected from the unmounted portion 24 of the membrane 14.

Analyte Collection

In an exemplary embodiment of the LFT device 10, running the LFT assay collects a portion of the analyte 32, e.g., microorganism, from the sample 26 in the membrane 14. Immobilizing specific antibodies to the analyte 32 in the LFT device 10 can increase the analyte 32 collected. Antibodies can be immobilized in a number of combinations on either the conjugate pad 18 or the membrane 14, which can satisfy current and/or future technical requirements, applications or special demands of the market.

To increase the likelihood for a true positive result, rather than a false negative, by the analysis technique, such as PCR or ELISA, the punch 48 is obtained from a high yield area of the membrane 14. The high yield areas for the punch 48 include the membrane 14 in the test line 40 (as seen in FIGS. 4B and 5C) that is positive by immunoassay.

In other words, another embodiment includes the LFT device 10 further includes at least a biologic marker, in which the biologic marker is configured to concentrate the analyte 32 in a predetermined sample collection region (such as the test line 40 that is positive, or other biologic marker location) by an assay format chosen from a group consisting of direct, competitive, and boulder in the stream. Another embodiment can include the biologic marker is a specific antibody targeted to the analyte 32.

Another high yield area of the membrane 14 for the punch 48 is a first portion 52 of the unmounted portion 24 of the membrane 14, as seen in FIG. 6. The best location to take the punch 48 is the first 2 mm of the membrane closer to the sample pad 12. The sample 26 becomes more filtered by sampling within the membrane 14 closer to the wick 16. In an exemplary embodiment, the first portion 52 is the first 5 mm of the unmounted portion 24 closest to the sample pad 12, when the unmounted portion 24 length (identified as 54) is 20 mm and width (identified as 56) is 4 mm. In a further exemplary embodiment, the membrane 14 is sampled within the first 2 mm of the unmounted portion 24 nearest the sample pad 12.

Method for Analysis of Analyte Including Lateral Flow Technology Device

An LFT device used in a method for analysis of the analyte 32 is provided. An exemplary method for preparing the sample 26 has at least the steps of grinding a plant tissue sample, performing the LFT assay with the LFT device 10, and taking a sample disc 48 from the LFT device 10 for use in an analytic system. Then, the step of analyzing the analyte 32 in the analysis system is performed.

The preparation of the sample 26 can be performed with the following materials:
  1×PBST (Phosphate buffer saline tween-20);
  Sample mesh bag (Agdia ACC 00930 or alternative);
  Tissue Homogenizer (Agdia ACC 00900 or alternative);
  the LFT device 10;
  1.5 ml Eppendorf PCR tube;
  and the puncher (e.g., Whatman® Harris Uni-Core™ 1.2 mm) for obtaining the punch 48.

The step of grinding of the plant tissue can be performed by the following steps:
  1. Determine the exact amount of plant tissue and 1×PBST buffer needed. 1 g of plant tissue requires 10 ml of 1×PBST. Thus, 0.5 g plant tissue needs 5 ml of 1×PBST.
  2. Place the required volume of 1×PBST into a sample mesh bag (Agdia ACC 00930 or alternative).
  3. Add the measured amount of plant tissue inside the sample mesh bag containing the 1×PBST. Make sure the plant tissue is between the mesh inside the bag and located near the bottom of the bag.
  4. Slightly fold the opening of the bag to prevent spilling while grinding the plant tissue inside the bag using a tissue homogenizer (Agdia ACC 00900 or alternative).
  5. Grind the plant tissue until the tissue is completely macerated and the extracted solution becomes translucent.

The step of performing the LFT assay with the LFT device 10 can be performed with the cassette 58 or without the cassette 58. When using the LFT device 10 without the cassette 58, pipette 0.5 ml of the extracted solution into a 1.5 ml Eppendorf tube. Place the sample pad 12 of the LFT device 10 in the extracted solution in the Eppendorf test tube and allow the solution to move upward until it reaches the wick (~3 minutes.). After the flow migration, remove the LFT device 10 from the Eppendorf tube. Subsequently, take the punch 48 from the membrane 14 of the LFT device 10. Subsequently, either obtain a 1.2 mm sample disc 48 or allow the membrane to dry in a clean Petri dish for 3 to 10 minutes. This 3 to 10 minutes drying is optional because the assay works well in both ways wet or dry. However, when the soluble paper is dry it might be easier to punch and manipulate and some user would prefer to wait, but it works well in both ways.

When using the LFT device 10 inside the cassette 58, pipette 0.5 ml of the extracted solution into the well 72 of the cassette 58, then allow the extracted solution to flow towards the wick (~3 minutes). Subsequently, take the punch 48 from the membrane 14 of the LFT device 10. Subsequently, either obtain a 1.2 mm sample disc 48 or allow the membrane to dry in a clean Petri dish for 3 to 10 minutes.

The step of taking sample disc 48 from the LFT device 10 for analysis, such as by the PCR or ELISA technique, can be accomplished by the following steps:
  1. Take 1.2 mm sample disc 48 from the membrane 14 by punching it out using a puncher (e.g., Whatman® Harris Uni-Core™ 1.2 mm or alternative).
  2. Place the punch 48 directly into a tube for PCR or a ELISA microplate well.

Then, the PCR or ELISA based assay is performed according to any appropriate PCR or ELISA protocol.

Exemplary Water Soluble Biomaterial

A series of experiments were carried out to assess the physical properties of a variety of water soluble biomaterial ("WSB") that can be used for the membrane 14 in the LFT device 10. The WSB used for the experiments were obtained from Aquasol® Corporation (North Tonawanda, N.Y.). The WSB are identified by Aquasol® as ASW-15, ASW-25, ASW-50, ASW-DC, and ASW-240. The thickness of ASW-15 is 50 µm. The thickness of ASW-25 is 83 µm. The thickness of ASW-50 is 76 µm. The thickness of ASW-DC is 50 µm. The thickness of ASW-240 is 170 µm.

Figure 9:
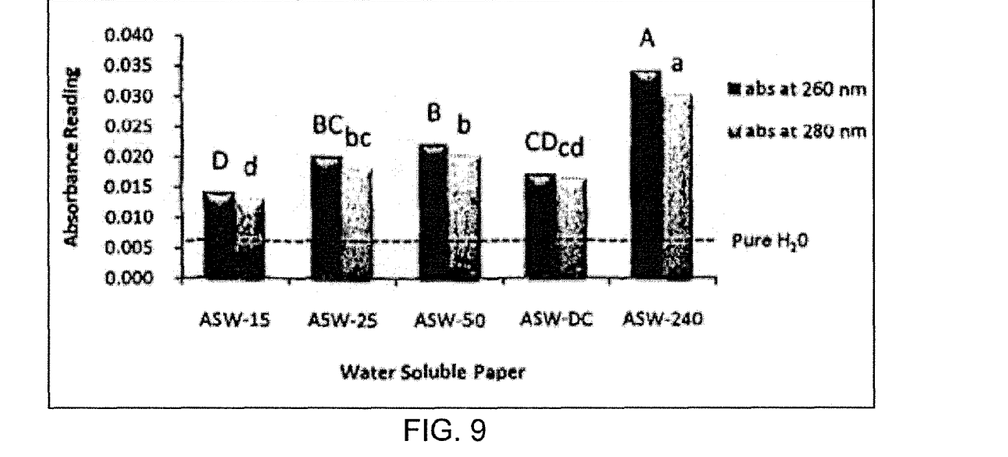
FIG. 9 is a graphic representation of absorbance readings for different water soluble papers.
Figure 10:
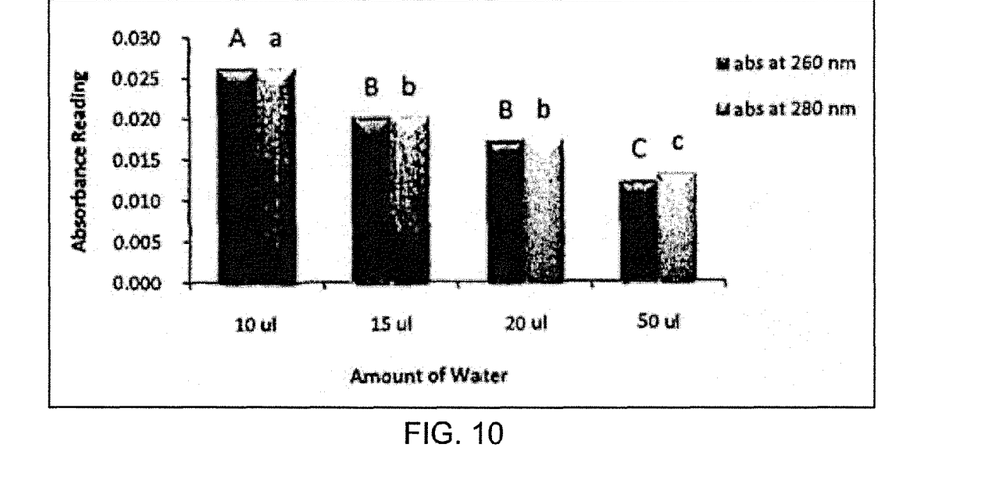
FIG. 10 is a graphical representation of absorbance readings for different amounts of water.

In Experiment 1, 10 µl, 15 µl, 20 µl, & 50 µl of water were placed on WSB. An ANOVA (Factor 1: WSB and Factor 2: amount of water) and Duncan's Multiple Range Test for absorbance readings at 260 nanometers ("nm") and 280 nm was performed. ASW-15, ASW-25, ASW-50, ASW-DC, and ASW-240 were tested. Water was used as control. The amount of water used was 10 µl, 15 µl, 20 µl, and 50 µl. The thickest material had more residues as measured by the highest absorbance, as shown in FIGS. 9 and 10.

Figure 11:
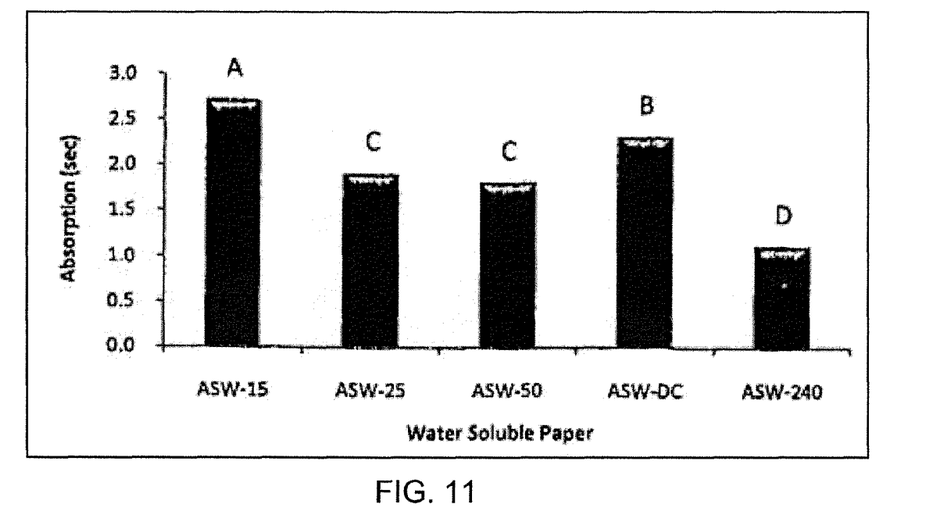
FIG. 11 is a graphical representation of absorption times for different water soluble papers.
Figure 12:
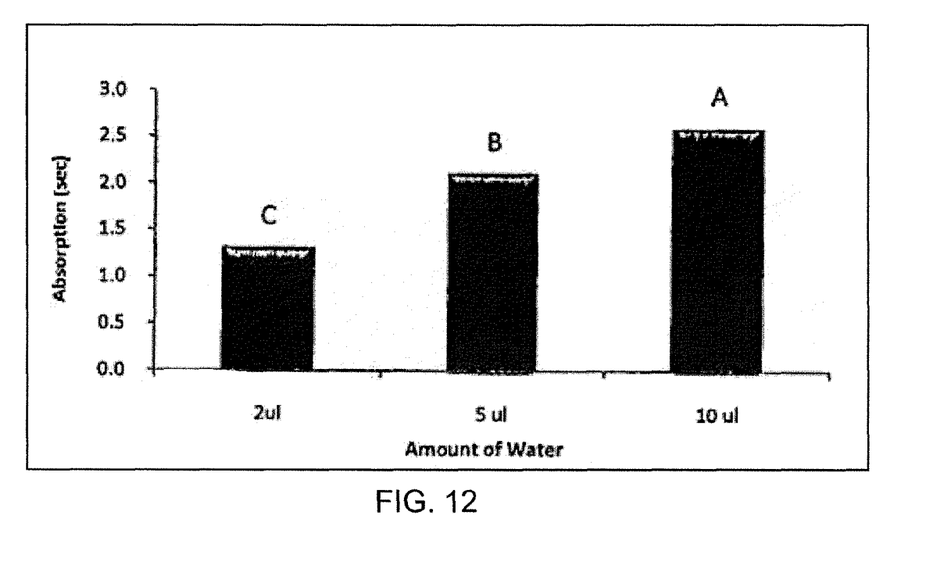
FIG. 12 is a graphical representation of absorption time for different amounts of water.

In Experiment 2, a predetermined amount of water was applied to a predetermined amount of WSB. 2, 5, and 10 µl of water were placed on WSB surface. An ANOVA (Factor 1: WSB and Factor 2: amount of water) and Duncan's Multiple Range Test for absorption time was performed. ASW-15, ASW-25, ASW-50, ASW-DC, and ASW-240 were tested. The 
amount of water used was 2 µl, 5 µl, and 10 µl. The thickest WSB absorbed water faster than the thinnest WSB and the more water was applied to the WSB the slower the applied water was absorbed, as shown in FIGS. 11 and 12.

In Experiment 3, a predetermined amount of water was applied to a WSB. An ANOVA (Factor 1: WSB and Factor 2: amount of water) and Duncan's Multiple Range Test for water spot diameter was performed. ASW-15, ASW-25, ASW-50, ASW-DC, and ASW-240 were tested. The amount of water used was 2 µl, 5 µl, and 10 µl. The more water was applied to the WSB the larger was the spot. No holes were made in the WSB with any of the water volumes tested wherein "holes" is defined as a perforation, fissure, crack or fiber gap visible to the naked eye.

In Experiment 4, the objective was to determine surface appearance, i.e., changes in a matrix of porosity, of WSB and compare "dry" WSB versus "wet" WSB; and to assess WSB for the presence of pore spaces that may serve as storage pockets for the analyte 32, such as microorganisms and nucleic acids. ASW-15, ASW-25, ASW-50, ASW-DC, and ASW-240 were tested. For the "dry" WSB, a small piece of WSB was selected and treated with Gold/Palladium (Au/Pd) coating as known to one skilled in the art. For the "wet" WSB, 10 µl of $H_2O$ was applied to the WSB and allowed to dry. Then, a small piece of WSB was selected and treated with Gold/Palladium (Au/Pd) coating as known to one skilled in the art. The samples of membranes used for SEM analysis were of square pieces of 13 mm×13 mm. Quanta 600F Field Emission Gun Scanning Electron Microscope ("SEM") (Hillsboro, Oreg.) was used to analyze the "dry" WSB and "wet" WSB at magnification=100×, Spot=3.0, and HV 10.00 kV. Under SEM, the organization of the fibers in the "wet" WSB is more scattered than in the "dry" WSB, and wetting the WSB caused changes in the physical structure of the WSB such that potential storage pockets are present. Measure of porous size were done and there were not dramatic changes after wetting.

Fixation of Analytes in Water Soluble Biomaterial

In Experiment 5, the objective was to fix an analyte 32 in a storage pocket in the WSB and view the fixed analyte and the storage pocket under SEM. ASW-15, ASW-25, ASW-50, ASW-DC, and ASW-240 were tested. The exemplary analyte 32 was a bacteria, specifically *Pseudomonas syringae* pv. tomato DC3000.

The exemplary method steps of a process for a protocol used for fixation of the bacteria to the WSB is commenced at step 5A by treating a WSB with 10 μl of a bacterial culture of *Pseudomonas syringae* pv. tomato DC3000.

In common practice by one skilled in the art, a fixation procedure for the analyte 32 includes soaking the analyte 32 and the membrane 14 in a series of reagents; however, the WSB is soluble so "dropping" 25 μl of the reagents was done instead.

At step 5B, dropping 25 μl of 2% glutaraldehyde onto the WSB treated area acts as a primary fixation, and the glutaraldehyde was let stand for 45 minutes.

At step 5C, dropping 25 μl of 0.1M phosphate buffer onto the WSB treated area cleans the treated area, and the phosphate buffer was let stand for 20 minutes. Process step 5C is repeated before moving onto process step 5D.

At step 5D, dropping 25 μl of 1% $OsO_4$ solution onto the WSB treated area acts as a secondary fixation, and the phosphate buffer was let stand for 45 minutes.

At step 5E, dropping 25 μl of 0.1M phosphate buffer onto the WSB treated area cleans the treated area, and the phosphate buffer was let stand for 20 minutes.

At step 5F, performing a series of dehydration stages on the WSB treated area by dropping 30% EtOH and letting stand for 15 minutes, then dropping 50% EtOH and letting stand for 15 minutes, then dropping 70% EtOH and letting stand for 15 minutes, then dropping 90% EtOH and letting stand for 15 minutes, then dropping 95% EtOH and letting stand for 15 minutes, and then dropping 100% EtOH and letting stand for 15 minutes, and then dropping on the WSB treated area once again 100% EtOH and letting stand for 15 minutes.

Under SEM, the analyte 32, which in this experiment is bacteria, was found on a surface or the storage pockets of the ASW-15, ASW-25, and ASW-240. ASW-25 provided the best fixation images under SEM. No bacteria were found on the surface or storage packets of the ASW-50 and ASW-DC. In addition, "salt" particles were detected in some SEM images. Without being bound by the theory, the "salt" particles were possibly present on the SEM images because the fixation procedure was performed by dropping reagents onto the WSB rather than soaking the WSB.

PCR Analysis Using Water Soluble Biomaterial

A series of experiments were carried out to determine whether the WSB substantially inhibits with PCR reactions when the analyte 32 bound to the membrane 14 of the LFT device 10 is placed in the analysis system for PCR analysis. ASW-15, ASW-25, ASW-50, ASW-DC, and ASW-240 were tested. A Microfuge i.e., a "bench top centrifuge," (Beckman Instruments, Inc.; Eppendorf, centrifuge 5418) was used. A PCR machine, namely PTC-200 Thermo Cycler (MJ Research, Inc.), was prepared. A puncher (Whatman® Harris Uni-Core™) was used to obtain discs for PCR amplification.

In Experiment 6, the objective is to determine whether the WSB substantially inhibits with PCR reactions. The exemplary method steps of a protocol for PCR analysis using analyte 32 fixed to the WSB is commenced. The exemplary analyte was a viral ds-RNA (double strand RNA), specifically CiLV-C (Citrus leprosis virus C) at 400 ng/μl concentration. Step 6A includes spotting 1 μl of a viral RNA on the WSB is performed.

Step 6B includes obtaining 1.2 mm disc of the viral spotted WSB. Step 6C includes adding the 1.2 mm disc of each of the viral spotted WSBs to a separate PCR test tube containing RT-PCR reaction mix. The exemplary 20 μl of RT-PCR reaction mix:

sterile nuclease-free water, 3.2 μl;

2× Reaction mix (Invitrogen), 10.0 μl;

RNAsin Plus 40 U/μl, 1.0 μl;

5 μM Forward Primer, 2.0 μl;

5 μM Reverse Primer, 2.0 μl;

SuperScript™ III One-Step RT-PCR System with Platinum® Tag DNA Polymerase (Invitrogen™ 12574-026) Mix, 0.8 μl;

and albumin from bovine serum (SIGMA-ALDRICH® A7888) at 10 μg/μl, 1.0 μl.

Thus, each test tube for the RT-PCR reaction contains 20 μl of RT-PCR mix and the 1.2 mm disc of the viral spotted WSB.

In Step 6D, there is running a RT-PCR reaction under the conditions, as shown in the table 1 below:

TABLE 1

| Step | Temperature | Time | Number of Cycles |
|---|---|---|---|
| cDNA synthesis | 50° C. | 30 minutes | 1 |
| Initial denaturation | 94° C. | 2 minutes | 1 |
| Denaturation | 94° C. | 30 seconds | 40 |
| Annealing | 56° C. | 30 seconds | |
| Elongation | 72° C. | 30 seconds | |
| Final Elongation | 72° C. | 7 minutes | 1 |

In Step 6E, there is loading PCR products from each test tube from the reverse transcription PCR (RT-PCR) reaction in separate preparations of 1.0 to 2% Agarose gel in 1×TBE (Tris base, boric acid and EDTA) and running electrophoresis on the PCR products for 90 minutes at 90 Volts. Visualization was made by incorporating SYBr green to the agarose gel. The observation was made upon ultraviolet (UV) light.

Amplification by RT-PCR was successful using the viral spotted ds-RNA as the PCR template. In other words, the WSB does not substantially inhibit the PCR reaction.

In Experiment 7, the objective is to determine whether the WSB substantially inhibits PCR product quantification. ASW-25, ASW-50, and ASW-DC were tested.

The exemplary method steps of a protocol for PCR product quantification using analyte fixed to the WSB is commenced. Step 7A is loading 2 µl of PCR product from Experiment 6 in the NanoDrop® ND-1000 Spectrophotometer (Thermo Scientific of Wilmington, Del.), Nucleic Acid—DNA option for each PCR product produced from each WSB. Step 7B is quantifying each PCR product produced from each WSB. The DNA quantification results were ASW-25, 379.7 ng/µl; ASW-50, 384.8 ng/µl; and ASW-DC, 365.9 ng/µl for. Recall that the viral ds-RNA tested was CiLV-C, 400 ng/µl. Thus, the WSB does not substantially inhibit the PCR reaction technique for quantification of PCR reaction product.

In Experiment 8, the objective is to determine what concentrations of DNA fixed to WSB can be amplified by PCR. ASW-15, ASW-25, ASW-50, ASW-DC, and ASW-240 were tested. The template is *Pythium spinosum* ("PS-1"), 10 ng/µl.

The exemplary method steps of a protocol for serial dilution of DNA template and testing PCR amplification sensitivity is commenced. Step 8A is transferring 10 µl to PS-1 to a test tube A. Step 8B is transferring 1 µl from the test tube A to a test tube B that has 9 µl of H$_2$O for 10 µl total volume in test tube B. Step 8C is transferring 1 µl from the test tube B to a test tube C that has 9 µl of H$_2$O for 10 µl total volume in test tube C. Step 8D is transferring 1 µl from the test tube C to a test tube D that has 9 µl of H$_2$O for 10 µl total volume in test tube D. Step 8E is transferring 1 µl from the test tube D to a test tube E that has 9 µl of H$_2$O for 10 µl total volume in test tube E. Step 8F is transferring 10 µl of H$_2$O to a test tube F. Steps 8A to 8F are repeated for each WSB tested.

At step 8G, 1 µl from each of the test tubes 8F is spotted on the WSB. Step 8G is repeated for each WSB tested.

At step 8H, a 1.2 mm disc of the spotted WSB area is taken by the puncher. Step 8H is repeated for each WSB tested.

Step 8I is adding each of the 1.2 mm discs from each of the spotted WSB to separate PCR test tube for each spotted WSB sample. The control has no WSB and 1 µl plasmid DNA for each concentration. The exemplary 20 µl of RT-PCR reaction mix:
sterile nuclease-free water, 8 µl;
GoTaq mix (Promega Corporation, Madison, Wis.), 10 µl;
10 µM Forward Primer, 1 µl; and
10 µM Reverse Primer, 1 µl.

In Step 8J, there is running a RT-PCR reaction under the conditions, as shown in table X, for each separate PCR test tube for each spotted WSB sample.

In Step 8K, there is loading PCR products from each test tube from the RT-PCR reaction in separate preparations of 1.0% Agarose gel and running electrophoresis on the PCR products for 90 minutes at 90 Volts.

As shown in Table 2 below, ASW-15, ASW-25, and ASW-50 did not interfere with PCR amplification up to the fourth dilution.

TABLE 2

| | Sample | | | | | |
|---|---|---|---|---|---|---|
| Tube | ASW-15 | ASW-25 | ASW-50 | ASW-DC | ASW-240 | Positive CONTROL |
| A | + | + | + | + | + | + |
| B | + | + | + | + | + | + |
| C | + | + | + | + | + | + |
| D | + | + | + | + | − | + |
| E | + | + | + | − | − | − |
| F (negative control) | − | − | − | − | − | |

The + signifies a positive result, i.e., PCR amplification successful. The − signifies a negative result, i.e., PCR amplification unsuccessful. The F test tube was a negative control for each of ASW-15, ASW-25, ASW-50, ASW-DC, and ASW-240, i.e., tube F is the negative control, it is required to demonstrate the WSB is not reactive or contaminated.

Exemplary Sample Pad Materials

After the format for the LFT device 10 was developed as shown in FIG. 7, a series of experiments were conducted to search for the best material for the sample pad 12. The sample pad 12 and the wick 16 were made from the same material. The membrane 14 was made from ASW-25. The sample pads 12 were 26 mm long. The membranes 14 were 25 mm long. The wicks 16 were 21 mm long. The sample pads 12, the membranes 14, and the wicks 16 were 4 mm wide. The holder 46 was provided of length 8 mm on the backing card of 75 mm length and 4 mm width. See FIG. 7 for length and width orientations. A test solution of 1×PBST 500 µl with 15 µl dye was used.

The objective of Experiment 9 was to determine which materials tested would produce fast flow through the LFT device 10. The materials tested for the sample pad 12 included: Ahlstrom (Helsinki, Finland) 1660, 1662, 1663, 6615; Millipore (Billerica, Mass. USA) C048, C0083, G041; and Whatman (Whatman plc, UK) 16-S, 470, 2668, 2727, CF6, Fusion 5™ GF33, GB002, GF/D, Standard 17. ASW-15, ASW-25, ASW-50, ASW-DC, and ASW-240 were also tested for the sample pad 12, although it was found that making the sample pad 12, the membrane 14, and the wick 16 from a single continuous piece was impractical, because the bottom part of the continuous piece that soaked in the test solution dissolved and mixed in the solution. Millipore C083; and Whatman GF33, GB002, and Standard 17 were good candidates for the sample pad 12 with wicking rate less than 4 minutes. In an exemplary embodiment, the less than 4 minute is preferable to reduce the possibility that the WSB in the membrane, in this case ASW-25, will dissolve in the solution during the wicking process.

In experiment 10, the four candidate materials for the sample pad 12 were tested again. Millipore C083 had the lowest wick rate and the smallest standard deviation when each of the good candidates were tested 10 times each; therefore, Millipore C083 was selected for the sample pad 12 in the LFT device 10 in one other exemplary embodiments. The Millipore C083 wicking rate mean is 2.9417 minutes. The Whatman Standard 17 wicking rate mean is 3.2266 minutes. The Whatman GB002 wicking rate mean is 3.7321 minutes. The Whatman GF33 wicking rate mean is 3.7928 minutes.

In other words, an exemplary embodiment includes a method comprising, the steps of: flowing a sample 26 solution that contains an analyte 32 through an LFT device 10 configured to bind the analyte 32; punching a sample disc 48 that binds the analyte 32 from the LFT device 10; and placing the sample disc 48 directly in an analysis system for analysis of the analyte 32, in which the step of placing the sample disc 48 is not preceded by a step of eluting the analyte 32 from the sample disc 48. A second embodiment includes the LFT device 10 includes at a least water soluble paper that binds the analyte 32, and the sample disc 48 is punched from the water soluble paper. A third embodiment includes the analysis system includes at least an analysis technique selected from a group consisting of polymerase chain reaction ("PCR"), and the initial denaturation is a predetermined prolonged interval selected to promote the PCR. A fourth embodiment includes the step of flowing a sample 26 solution is preceded by at least the steps of: measuring a predetermined amount of a sample 26 material; calculating a volume of a solution responsive to the predetermined amount of the sample 26 material; providing a sample bag to which the volume of the solution is added; adding the predetermined amount of the sample 26 material to the solution in the sample bag; and grinding the sample 26 material in the bag until it is macerated and the solution is translucent to prepare the sample 26 solution.

While the invention has been described in connection with an exemplary embodiment, it is not intended to limit the scope of the invention to the particular form set forth, but on the contrary, it is intended to cover such alternatives, modifications, and equivalents as may be included within the spirit and scope of the invention as defined by the appended claims.

It will be clear that the present invention is well adapted to attain the ends and advantages mentioned as well as those inherent therein. While presently preferred embodiments have been described for purposes of this disclosure, numerous changes may be made which will readily suggest themselves to those skilled in the art and which are encompassed by the appended claims.

What is claimed is:

1. An apparatus comprising:
   a backing card;
   a sample pad adhered to said backing card;
   a wick adhered to said backing card and spaced apart from said sample pad;
   a water soluble membrane situated between said sample pad and said wick and in communication with both said sample pad and said wick, said membrane comprising an affixed portion and an unaffixed portion, said affixed portion being secured to said backing card such that said unaffixed portion is at least large enough to permit a punch to extract a sample therefrom without including any of said affixed portion in the sample, wherein there is a gap between at least a portion of said membrane and said backing card;
   wherein said membrane binds an analyte from a sample that flows through a flow path defined by said sample pad, through said membrane to said wick; and,
   wherein said unmounted portion of said membrane does not substantially inhibit analysis of the analyte when placed in an analysis system.

2. The apparatus of claim 1, wherein:
   said unmounted portion of said membrane is water soluble paper.

3. The apparatus of claim 1, wherein:
   said unmounted portion of said membrane includes at least sodium carboxy methyl cellulose.

4. The apparatus according to claim 1 further comprising:
   a housing surrounding said backing card, sample pad, wick and membrane to facilitate long term storage.

5. The apparatus of claim 1, further comprising:
   a biologic marker attached to said membrane concentrates said analyte in a predetermined sample collection region of said membrane by an assay format chosen from a group consisting of direct, competitive, and boulder in the stream.

6. The apparatus of claim 5, in which said biologic marker is a specific antibody targeted to said analyte.

* * * * *